United States Patent [19]
Eckerle et al.

[11] Patent Number: 5,176,143
[45] Date of Patent: Jan. 5, 1993

[54] TONOMETER TRANSDUCER POSITIONING SYSTEM

[75] Inventors: Joseph S. Eckerle, Redwood City; Roy D. Kornbluh, Palo Alto; Rudolf Elbrecht, Los Altos; Eric A. Edwards, Menlo Park, all of Calif.

[73] Assignee: Colin Electronics Company, Ltd., Hayashi, Japan

[21] Appl. No.: 716,116

[22] Filed: Jun. 17, 1991

[51] Int. Cl.⁵ ............................................. A61B 5/022
[52] U.S. Cl. .................................................... 128/677
[58] Field of Search ............... 128/668, 672, 675, 677, 128/679, 680, 681, 682, 683, 686, 687, 689, 690

[56] References Cited

U.S. PATENT DOCUMENTS

| | | | |
|---|---|---|---|
| 2,555,422 | 6/1951 | Scott et al. | 128/689 |
| 3,102,534 | 9/1963 | Bigliano et al. | 128/672 |
| 3,219,035 | 11/1965 | Pressman et al. | 128/672 |
| 3,738,356 | 6/1973 | Workman | 128/675 |
| 4,475,554 | 10/1984 | Hyndman | 128/677 |
| 4,658,829 | 4/1987 | Wallace | 128/672 |
| 4,784,152 | 11/1988 | Shinoda | 128/690 |
| 4,830,017 | 5/1989 | Perry et al. | 128/687 |
| 4,832,039 | 5/1989 | Perry et al. | 128/682 |
| 4,836,213 | 6/1989 | Wenzel et al. | 128/672 |
| 4,901,733 | 2/1990 | Kaida et al. | 128/687 |
| 4,966,156 | 10/1990 | Perry et al. | 128/677 |
| 4,987,900 | 1/1991 | Eckerle et al. | 128/672 |

FOREIGN PATENT DOCUMENTS 2-79904 12/1988 Japan .
9002512 3/1990 World Int. Prop. O. .......... 128/687

OTHER PUBLICATIONS

Tochikubo et al., "Measurements of Base Blood Pressure During Sleep and Its Clinical etc.", Jap. Cir. Journ., vol. 51, Oct. 1987.

Primary Examiner—William E. Kamm
Attorney, Agent, or Firm—Oliff & Berridge

[57] ABSTRACT

A tonometric blood pressure monitoring system is disclosed having a variable extension sensor assembly. The sensor assembly is connected to a central control unit through separable pod elements. Within the pod elements are a master cylinder and drive system for varying the extension of blood pressure sensor from the sensor assembly. The blood pressure sensor is mounted at the end of an sensor piston, the movement of which is guided on a central rod. The sensor assembly also includes a rolling bellows arrangement for providing a variable hold-down pressure between a cavity block and the sensor assembly housing. The blood pressure sensor is moved laterally, in one embodiment, to provide optimum lateral placement of the sensor with respect to a target source of blood pressure information such as the radial artery of the subject.

25 Claims, 11 Drawing Sheets

TONOMETER TRANSDUCER POSITIONING SYSTEM

FIELD OF THE INVENTION

This invention relates to noninvasive sensors for sensing physiological parameters and in particular to sensors wherein the sensing element is pressed against a body surface to detect pressure in tissue or blood vessels. The invention has particular utility with respect to tonometric blood pressure measurement or monitoring.

BACKGROUND OF THE INVENTION

Systems for continuously monitoring blood pressure noninvasively by tonometry have been developed. In such systems, a pressure sensor is held against a portion of the body at which there is a significant artery close to the skin surface. The sensing element is pressed against the skin surface with a sufficient force to partially compress (but not occlude) the underlying artery so that the pressure of the blood within the artery can be sensed by a pressure sensor.

It is desirable to optimize the amount of arterial compression so that accuracy of the pressure reading is assured. In order to so, it has been proposed to provide the sensor with systems for varying the hold-down pressure, that is, the pressure with which the sensing element is pressed against the skin. Such systems are shown in U.S. Pat. Nos. 4,836,213 and 4,987,900, the disclosures of which are incorporated by reference herein. Although such systems are useful for optimizing the sensed pressure pulse, the accuracy of readings can vary from patient to patient, depending upon the amount and compliance of the tissue between the sensor and the underlying artery and on other anatomical variations. Thus, while such a system may provide high accuracy and reliability for a healthy subject whose radius has a typical depression for the radial artery, less than optimum results may be achieved with a subject having an unusually-deep radial depression or who has a significant amount of tissue between the target artery and the skin at the point where the sensor is placed on the body (for example, an obese subject).

In order to overcome these difficulties, sensors have been proposed which incorporate additional systems for moving the sensor element relative to the underlying artery in order to improve pressure sensing. One such arrangement is described in an article entitled "Measurements of Base Blood Pressure During Sleep and Its Clinical Significance in Hypertensive Patients" by Osamu Tochikubo et al in the Japanese Circulation Journal, Vol. 51, October, 1987. Another sensor design employing this feature is shown in Japanese Published Patent Application 2-79904 published on Jun. 20, 1990. While such sensor arrangements may improve the accuracy of blood pressure measurements, these designs are relatively expensive to manufacture and thus are unattractive to be made in disposable form. Furthermore, these proposed sensors have not included provision for use of a multiple-element sensor which requires a very large number of electrical connections.

SUMMARY OF THE INVENTION

It is an object of the present invention to provide a sensor assembly for positioning a tonometric sensor optimally over a wide range of tissue conditions and types. A further object is to account for variations in subject anatomy.

It is a further object of the invention to provide a low cost, disposable sensor assembly. It is a further object of the invention to provide a sensor assembly that is relatively small and light-weight and is resistant to movement artifacts in the measured blood pressure.

In accordance with the invention, the sensor assembly includes a housing adapted to be mounted on a subject, the housing incorporating a system for varying hold-down pressure of a pressure sensor on the subject. The sensor assembly includes a pin-mounted transducer mounting member forming a part of a slave cylinder and driven by a master cylinder located away from the subject-mounted sensor assembly. The master cylinder is mounted in a separable pod or housing, one portion of which is associated with the subject-mounted sensor assembly and the other portion of which is associated with the central control and monitoring unit.

DETAILED DESCRIPTION OF THE PREFERRED EMBODIMENT

Figure 1:
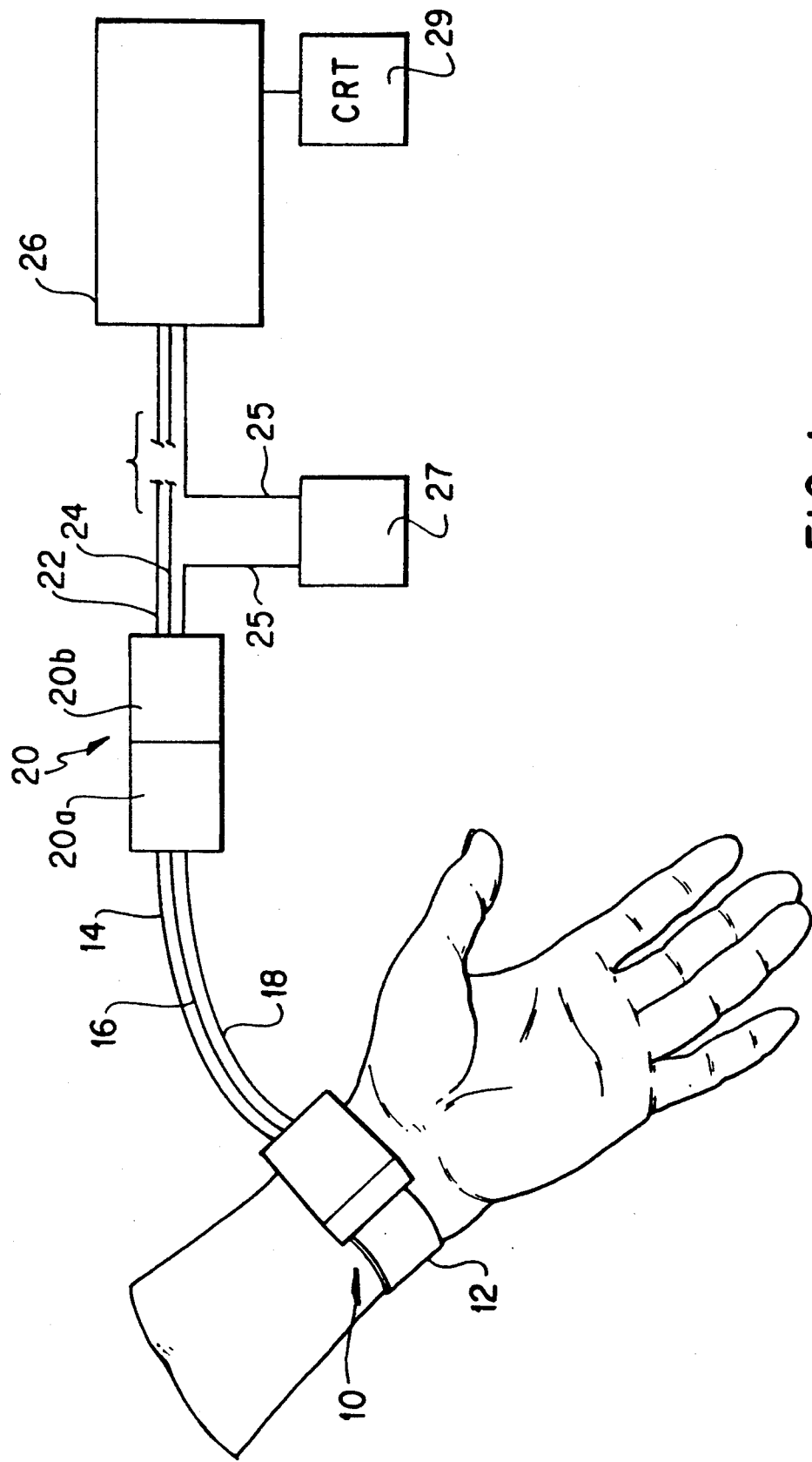
FIG. 1 shows the principal elements of a tonometric blood pressure monitoring system in accordance with the invention.

Referring to the drawings in more detail and to FIG. 1 in particular, the components of a tonometric blood pressure monitoring system are shown. As is conventional, the sensor assembly 10 is held on the wrist of the subject by a suitable means, such as strap 12, to sense blood pressure within the radial artery. The sensor assembly 10 is connected to an electrical lead 14, an air hose 16 and a hydraulic hose 18, which extend to a pod 20 that comprises two separable sections 20a and 20b. The section 20a is associated with the sensor assembly 10 and section 20b is associated with the central processing control unit 26. An electrical lead 22 and the flexible air line 24 extend from pod section 20b to the central unit 26.

The sections 20a and 20b of pod 20 are secured together by a securing means (not shown) allowing ready manual disassembly of section 20a from 20b. The details of such a securing means are within the skill of the art and no further explanation thereof is believed necessary. As will be explained more fully below, the electrical leads 14 and 22 provide for conducting of blood pressure signals from the sensor assembly 10 to the central unit 26 and are also used to conduct additional electrical control signals provided by or to electrical control components within the pod 20. Air lines 16 and 24 provide air under pressure for controlling the holddown pressure of the sensor assembly 10. Hydraulic line 18 provides hydraulic fluid for controlling the positioning of the pressure sensor or transducer, which senses blood pressure within the radial artery.

The monitoring system also includes electrical leads 25 extending from the pod 20 to a sensor controller 27 and from the sensor controller 27 to the central control unit 26. The sensor controller 27 includes control elements, such as manually settable counters and switches (not shown) for controlling extension and retraction of a pressure sensor relative to the sensor assembly 10, as will hereafter be described in more detail. The central control unit drives peripheral devices, such as CRT 29, via suitable converters, to display blood pressure readings or wave forms derived from the output of sensor assembly 10. The output of control unit 26 can also be used to drive other peripheral devices, such as microcomputers, for analyzing blood pressure signals, and printers, for providing a permanent copy of blood pressure measurements.

Figure 2:
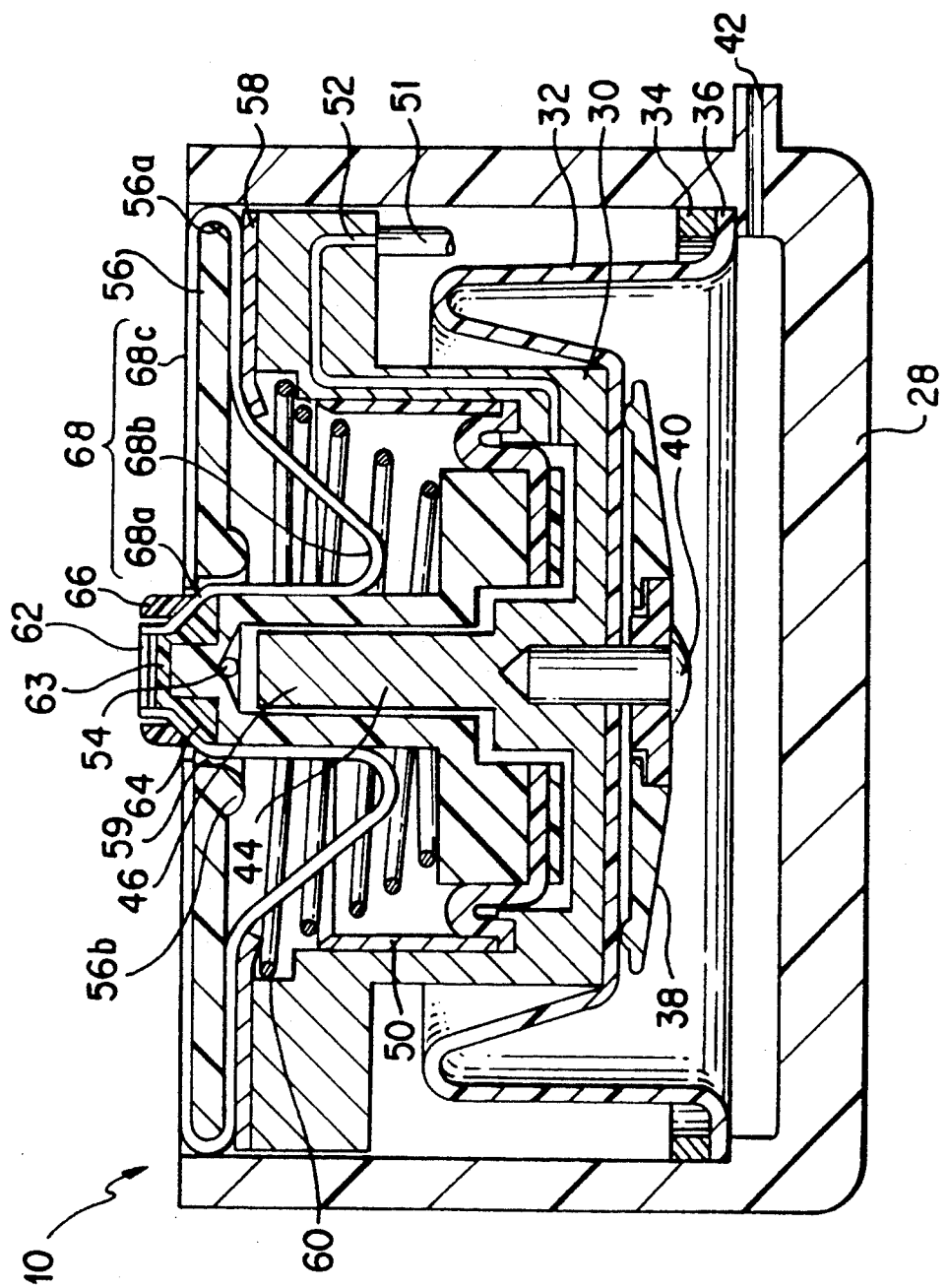
FIG. 2 is a cross-section of a sensor assembly with the pressure sensor in a retracted position.
Figure 3:
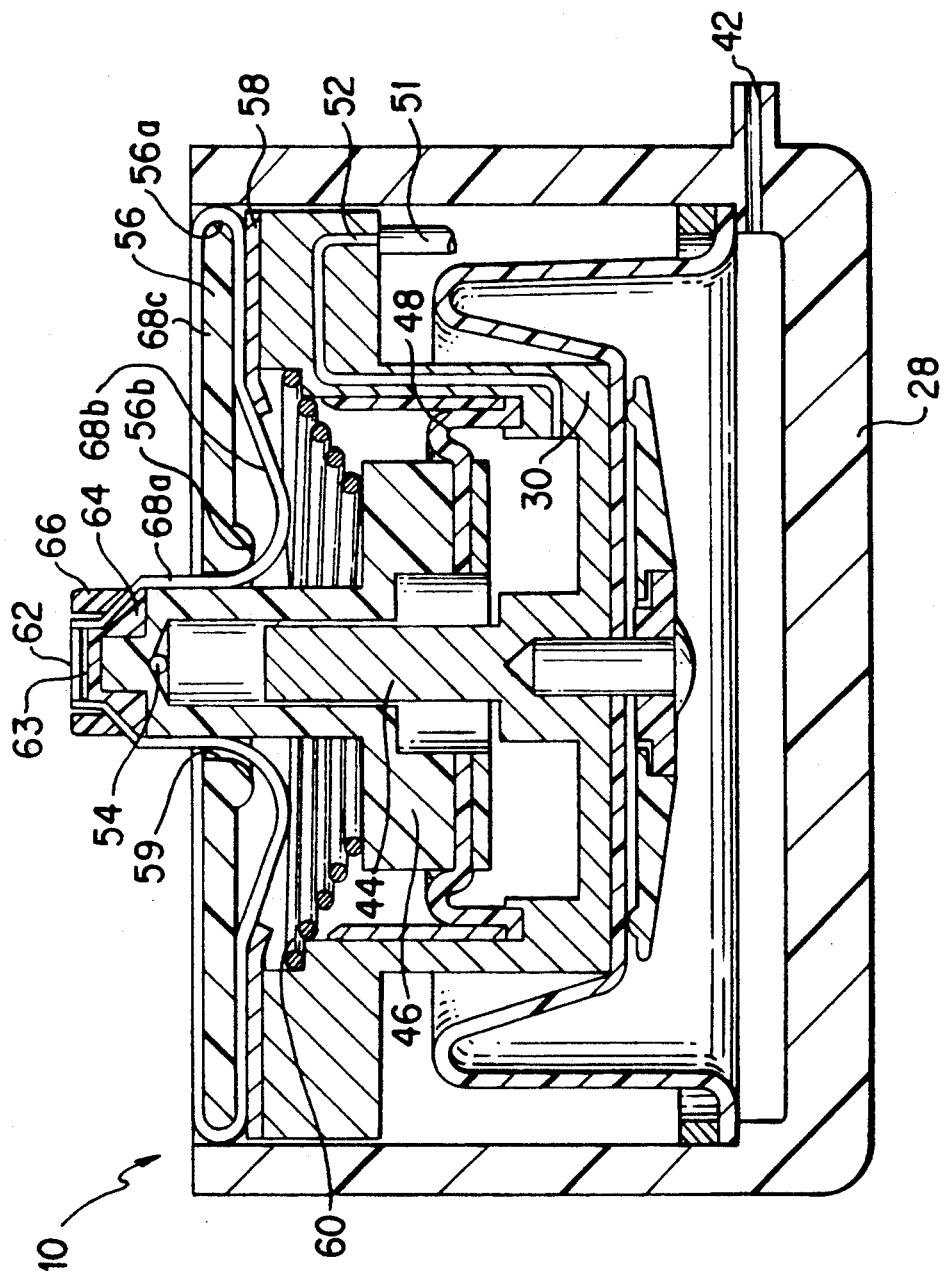
FIG. 3 is a cross-sectional view of a sensor assembly as shown in FIG. 2, with the pressure sensor in an extended position.
Figure 4:
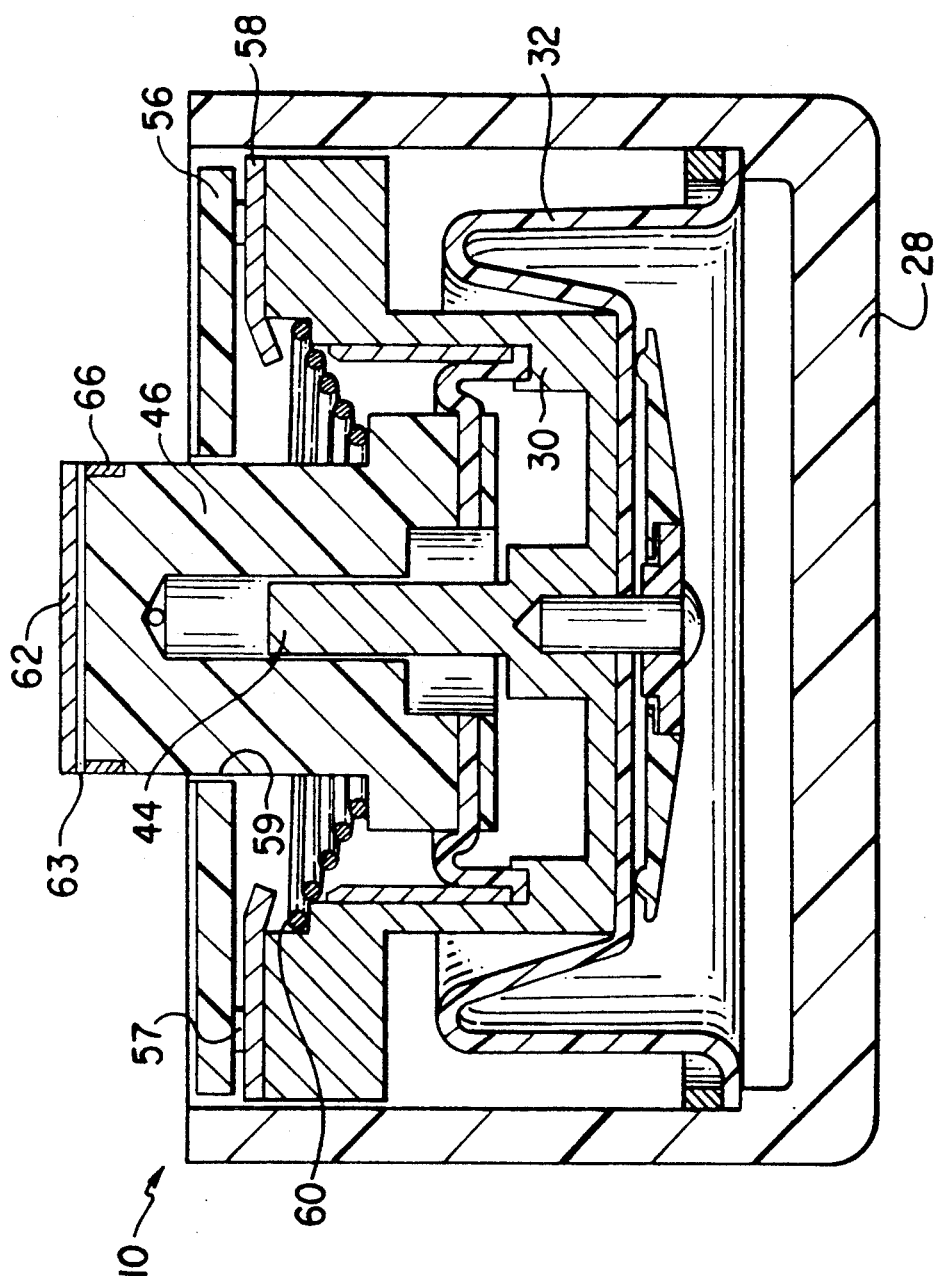
FIG. 4 is a cross-sectional view of a sensor assembly rotated 90° with respect to the cross-sectional views of FIGS. 2 and 3.

Referring to FIGS. 2, 3 and 4, the sensor assembly 10 includes a housing 28 in which is received a cavity block 30. The cavity block 30 is held within the housing 28 by means of a rolling bellows 32. The bellows 32 is retained in the housing 28 by a retaining ring 34, which holds the outer edge of the bellows 32 against a stepped surface 36 formed in the housing 28. The inner central portion of the bellows 32 is secured to the cavity block by means of a plate 38 which is secured onto the cavity block 30 by suitable means, such as a pin 40. The housing 28 is provided with a port 42 to which the air line 16 is attached. The port 42 communicates with a closed volume formed by the bottom portion of the housing 28 and the bellows 32, which is secured in the housing 28 in a fluid-tight manner by means of the retaining ring 34. By introducing air under pressure through the port 42, the cavity block 30 and its associated components can be urged in a direction outwardly of the housing 28. Because the housing 28 is secured on the subject by strap 12, varying the air pressure supplied to the port 42 varies the holddown pressure of the cavity block 30 against the wrist of the subject.

Referring again to FIGS. 2, 3 and 4, the cavity block 30 includes a centrally located cylindrical cavity and a substantially centrally located guide rod 44 extending from the bottom of the cavity. A sensor mounting member 46 is slidably received on the rod 44. Rod 44 acts to guide movement of the sensor mounting member 46 relative to the cavity block 30. The cavity block assembly includes a rolling bellows 48. The outer edge of the bellows 48 is securely held within the cavity block by suitable means, such as a spring-type retaining ring 50, which securely holds the outer edge of the bellows in the cavity block in a fluid-tight manner. The inner central portion of the bellows 48 is secured to the underside of the sensor mounting member 46. In this manner, a fluid-tight chamber is formed between the lower portion of the central cavity of the cavity block 30 and the sensor mounting member 46. A hydraulic fluid conduit 52, a portion of which is formed within the cavity block 30, provides fluid communication between the enclosed space formed by the bellows 48 and the cavity block 30 and the hydraulic line 18. A suitable length of flexible tubing 51 extends from the cavity block to a transition fitting (not shown), which is mounted on the housing 28 and to which the hydraulic hose 18 is attached. BY this arrangement movement of the cavity block 30 relative to the housing, as the cavity block moves by reason of changes in hold-down pressure or subject movement, is accomodated. The sensor mounting member 46 is also provided with a port 54 which is connected by suitable flow passages (not shown) formed in the sensor mounting member 46. Such passages provide fluid communication between the port 54 and the fluid-tight space formed between the bellows 48 and the bottom of the cavity in the cavity block 30. In this manner, fluid under pressure applied to the closed space beneath the bellows 48 is also supplied to the variable volume formed between the bore of the sensor mounting member 46 and the top of the rod 44. Thus, the fluid under pressure also acts between the distal end of the rod 44 and the portion of the bore of the sensor mounting member 46 extending above the rod.

The cavity block assembly also includes a retainer plate 58 disposed along the top edge of the cavity block 30. A spiral helical compression spring 60 extends between the retainer plate 58 and the sensor mounting member 46 to bias the sensor mounting member 46 toward a retracted position near the bottom of the cavity in the cavity block 30.

The cavity block assembly also includes a cover plate 56 which is secured by suitable means, such as screws 57 (FIGS. 4 and 5), onto the cavity block 30. A portion of the sensor mounting member 46 extends through an opening 59 in the cover plate 56.

As illustrated in FIG. 3, when hydraulic fluid under pressure is supplied via line 18 and conduit 52, the sensor mounting member 46 is urged out of the cavity block 30 to extend the mounting member 46 a greater distance outwardly of the cover plate 56. This movement takes place against the action of the spiral compression spring 60, which is compressed between the member 46 and the retaining plate 58. As previously mentioned, fluid under pressure provided to the space defined by the rolling bellows 48 and the bottom of the cavity block 30 is also provided by the port 54 to the volume formed above the distal end of rod 44.

A pressure sensing transducer 62 is positioned on the upper end of the sensor mounting member 46. The transducer 62 is of a known type having a plurality of individual pressure sensing areas disposed along its length. Such transducers are commonly formed as a microelectronic chip formed of silicon by known techniques. For example, a sensor chip as disclosed in U.S. Pat. No. 4,987,900, the disclosure which is incorporated herein by reference, could be utilized. Other transducers, wherein sensing elements are disposed on a common diaphragm formed in the chip, can also be utilized.

Figure 5:
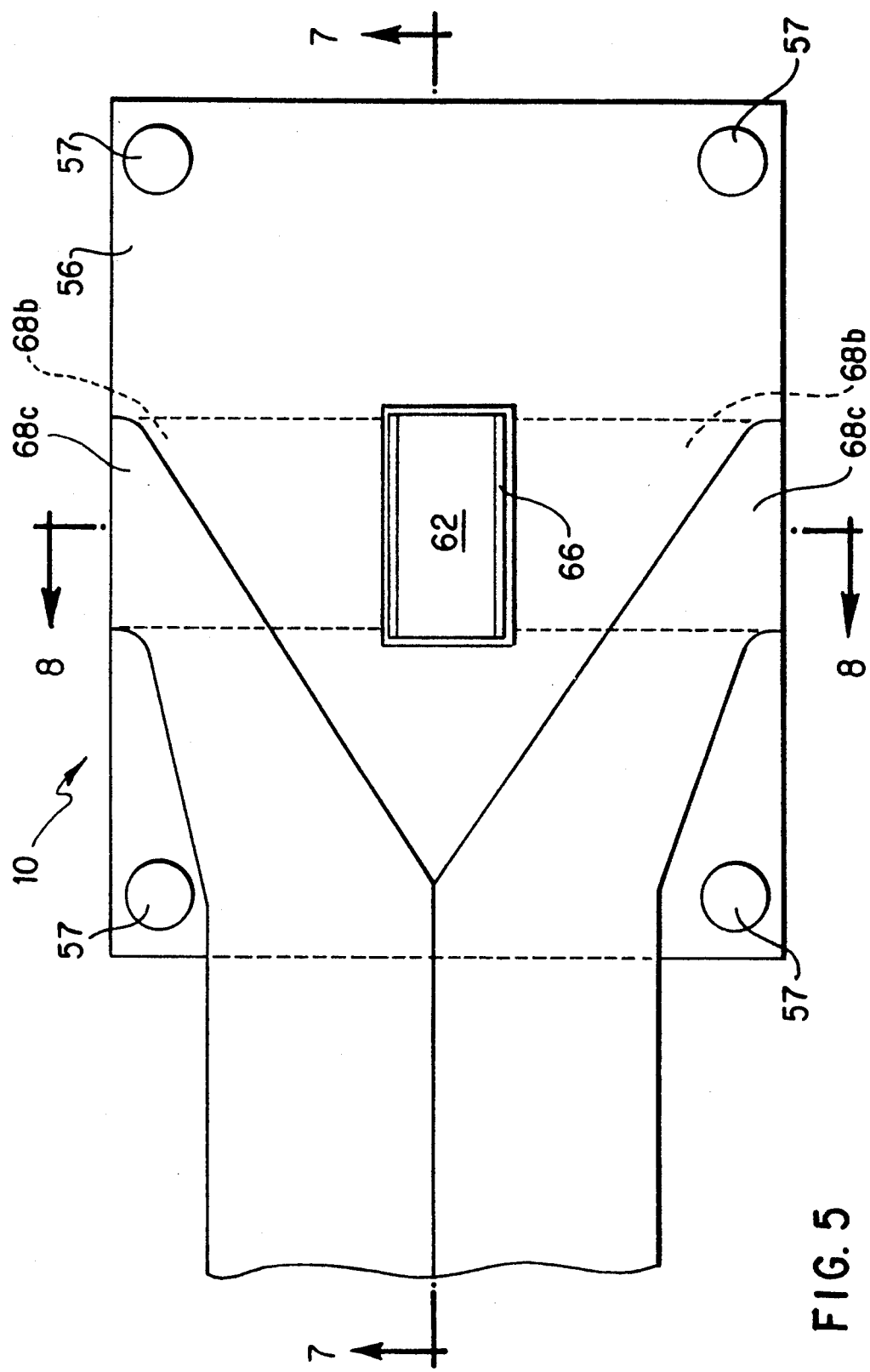
FIG. 5 is a top view of the sensor assembly shown in FIGS. 2, 3 and 4.
Figure 6:
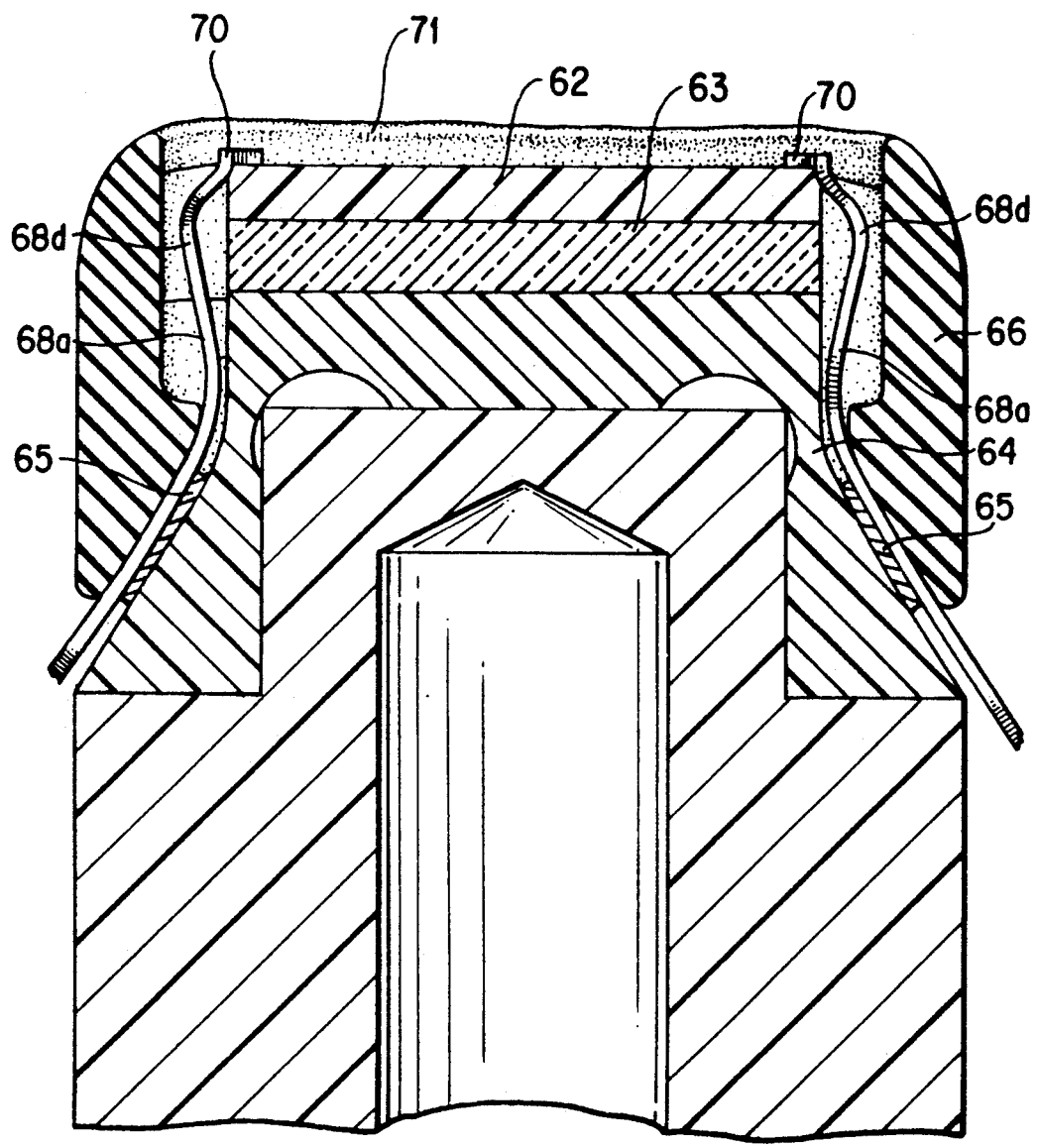
FIG. 6 is an enlarged view of the mounting of the pressure sensor.

As shown in FIG. 6, a layer 63 of glass is bonded to the bottom of transducer chip 62 as a base. The sensor consisting of the transducer chip 62 and glass base 63 is held on a sensor supporting cap 64 by suitable means, such as adhesives. Electrical connection to the chip 62 is provided by flexible conductors such as flexible printed circuits denoted by the reference numeral 68. The flexible printed circuits include first portions 68a connected to bonding pads on the upper surface of the chip and extending along the cap 64. A guard 66 extends along the side edges of the sensor and holds the printed circuit portion 68a against the cap 64. The first portion 68a of the flexible printed circuit 68 extends to a second portion 68b (FIG. 2), which is disposed in a loop beneath the cover plate 56 and within the area defined by the spiral helical compression spring 60. The looped portion 68b extends outwardly to the sides of the cover plate 56 and wraps about the radiused edges 56a to the third portion of the flexible printed circuit 68c, which extends along the top of the cover plate 56. Radiused surfaces 56b are also formed on the lower portion of the cover plate 56 surrounding the opening 59. The radiused portions 56a and 56b are provided so that the flexible printed circuit 68 does not engage or wrap about sharp edges which could damage the printed circuit. Referring to FIG. 5, the portions 68c of the flexible printed circuit wrap around outside edges of the cover plate 56 and extend along the top surface of the cover plate to an appropriate junction point or circuit element within the sensor assembly 10, such as a multiplexer (not shown). Alternatively, appropriate circuit connectors mounted on the edge 56a can be utilized to connect portions 68b to portions 68c.

In addition to the functions of the cover plate 56 described above, this structure has an important function relating to the interface of the device to the subject. Briefly, the cover plate 56 serves as a "reference surface", lying in a substantially fixed position with respect to the subject's radius (bone) and flexor carpi radialis tendon. This function is described in detail below.

As shown in FIG. 6, the flexible printed circuit guard 66 extends along side edges of the pressure sensing chip 62. The cap 64 preferably includes compressible clamping pads 65 for applying a uniform pressure to the flexible printed circuit portions 68a to maintain them fixed between the cap 64 and the guard 66.

The upper edges of the flexible printed circuit guard extend slightly beyond the height of the bonding pads 70 on the upper surface of the sensor chip. This configuration protects the pads from damage. An elastomeric coating 71 (such as silicone rubber) covers the surface of the pressure sensing chip and bonding pads. This coating protects the chip from abrasion and contamination by moisture or other chemicals. It also prevents damage to the patient's skin from sharp edges of the bonding pads and flexible printed circuit guard.

The flexible printed circuit is fabricated with a slight fold or undulation 68d located between the upper ends of portions 68a (where they are attached to the bonding pads 70) and the clamping pads 65. This feature eliminates undesirable loads on the chip that might adversely affect pressure measurements. For example, without this undulation, tensile stress in a diaphragm of the chip could be caused by the flexible printed circuit pulling on the bonding pads as a result of the assembly procedure or as a result of differential thermal expansion (of the flexible printed circuit, chip, and cap). Such tensile stress will greatly reduce the sensitivity of the chip, and also introduce "zero-shift" errors.

Figure 7:
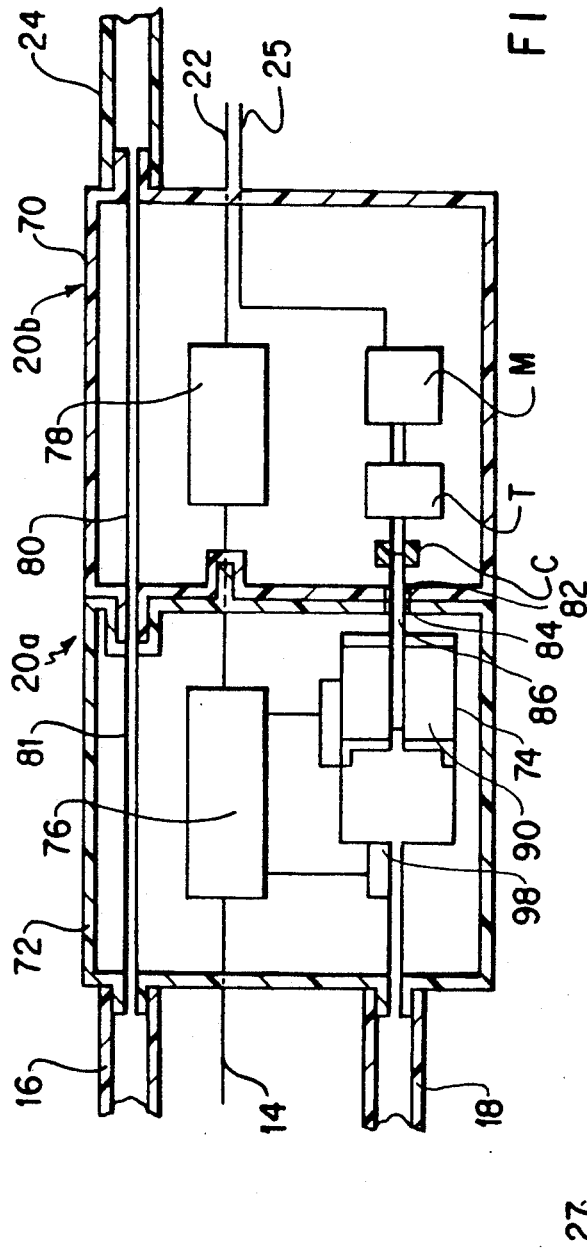
FIG. 7 is a cross-sectional view of a pod intermediate the sensor assembly and the control and monitoring unit.

Referring to FIG. 7, a cross section of the pod 20 is illustrated in schematic form. The pod 20 includes the separable sections 20a and 20b. As previously noted, the sections 20a and 20b are held together in a manner such that they can be easily manually separated or locked together. The section 20a is associated with the sensor assembly 10 and is connected thereto via the electrical lead 14, the flexible air line 16 and a flexible hydraulic line 18. Similarly, section 20b is connected to the central processing unit 26 via the electrical lead 22 and the flexible air hose 24.

A master cylinder 74 is mounted within the housing 72 of the pod section 20a. The master cylinder 74 includes a rotatable screw shaft 86 extending through an opening 84 in the wall of the housing 72 and through an opening 82 in the housing 70 to be slideably received in a drive coupling C. The coupling C is affixed to the end of an output shaft of a transmission T, the input to which, in the preferred embodiment, is a reversible stepper motor M. Rotation of the motor M drives the transmission T, which in turn drives the screw shaft 86 through the coupling C mounted on the output shaft of transmission T.

Figure 8:
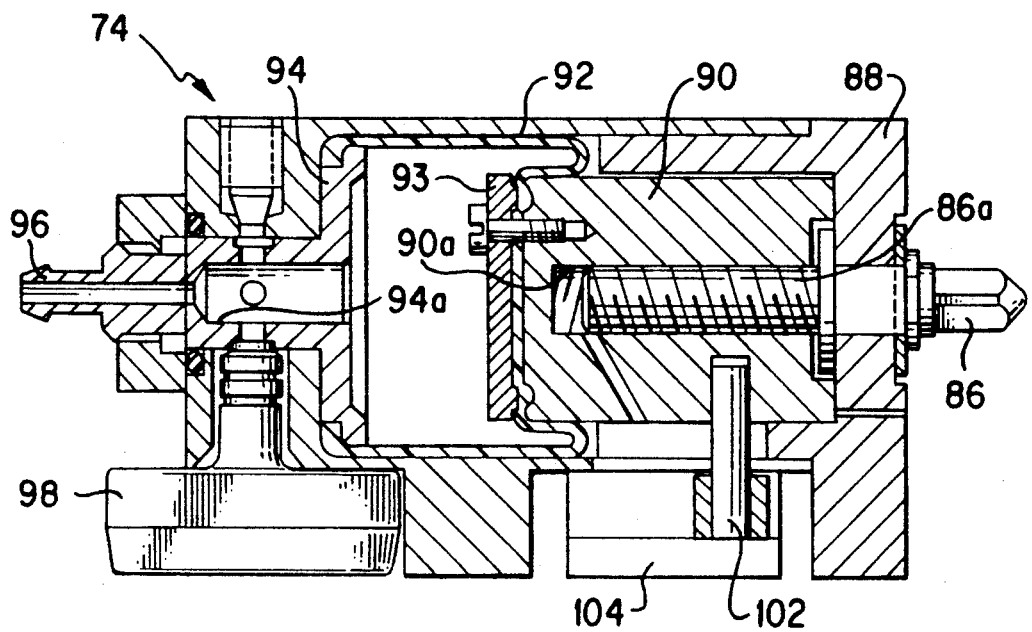
FIG. 8 is a cross-sectional view of a master cylinder for driving the sensor piston.
Figure 9:
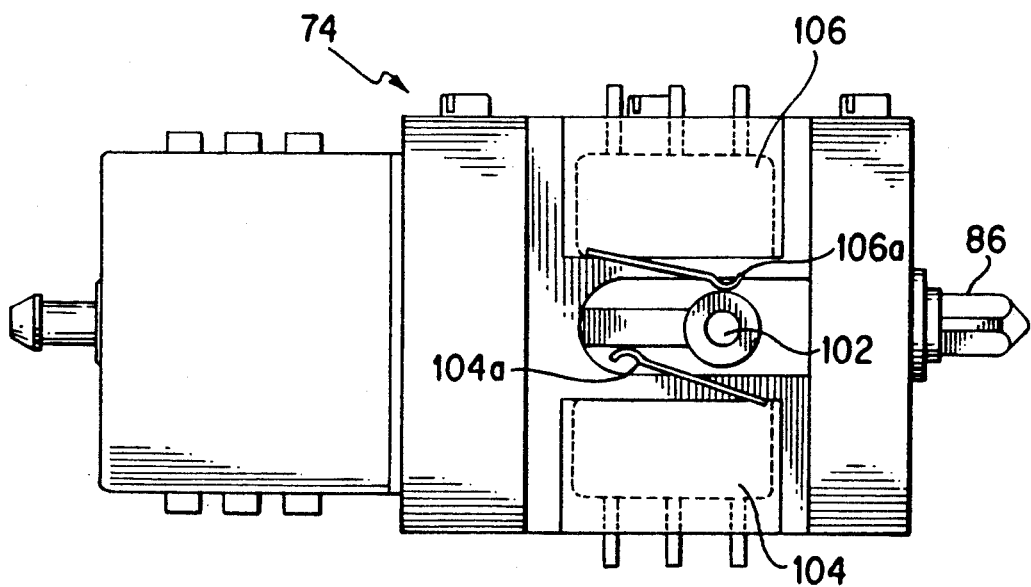
FIG. 9 is a bottom view of the master cylinder shown in FIG. 8.

Referring to FIGS. 8 and 9, the master cylinder 74 includes a master cylinder body having movably mounted therein a piston 90. A flexible rolling bellows 92 is fixed, at its central portion, to the front face of the piston 90. The outer edges of the bellows are secured in a fluid-tight manner to the master cylinder body by the port plate 94. The port plate 94 includes a fluid port 94a in fluid communication with the closed volume formed by the bellows 92 and the port plate 94. The plate 93 fixes the central portion of the rolling bellows onto the front face of the piston 90. The rotatable drive shaft 86 is mounted for rotation about its longitudinal axis in an end wall of the master cylinder body 88. The rotatable shaft 86 includes a threaded or grooved portion 86a at one end thereof. The threads or grooves of portion 86a engage with comparable threads or followers on an internal bore 90a of the piston 90. Rotation of the shaft 86 causes the piston to move longitudinally in accordance with the direction of rotation of the shaft 86. When the piston moves to left in FIG. 8, fluid within the chamber formed by the bellows 92 and the plate 94 passes through the port 94a and through the connector 96 to the hydraulic line 18 and is thereby supplied under pressure to the fluid cavity of the cavity block 30 of the sensor assembly. This results in advancement of the sensor mounting member out of the cover plate 56. Conversely, retraction of the piston 90 toward the right side of FIG. 8 draws fluid from the slave cylinder formed in the cavity block 30, thereby allowing the spring 60 to retract the sensor mounting member 46.

Pressure within the fluid system defined by the master cylinder and the slave cylinder is detected by a fluid pressure transducer 98. The output signal of the transducer 98 is provided to the central processing unit 26.

Referring to FIG. 9, a camming pin 102 is carried by the piston 90 and moves longitudinally in accordance with movement of the piston. The camming pin 102 is positioned to engage the actuators 104a and 106a of the limit switches 104 and 106, respectively. The actuators of limit switches 104 and 106 define the end points of travel of the piston 90 and, when actuated, provide control signals to prevent further driving of the shaft 86 by the motor M in one of the directions of travel.

Referring again to FIG. 7, electronic signal processing elements can be included in one or more sections 20a and 20b of the pod 20. For example, a multiplexer 76 can be included in the pod section 20a. The multiplexer 76 receives input signals from the pressure sensing transducer via the lead 14. As well, the multiplexer can receive signals from the fluid pressure transducer 98 and limitswitches 104,106, to provide control inputs for a microprocessor control system contained within the central processing unit 26. Alternatively, or in addition to signal processing circuitry 76, signal processing circuitry 78 can be included in the pod section 20b. In this circumstance, more sophisticated and costly processing circuitry would be included in pod 20b, which remains with the central processing unit 26. Less expensive elements would be included in the pod section 20a which can be made disposable, along with the sensor assembly 10.

Air pressure for varying the hold-down pressure of the sensor assembly 10 is provided by air conduits 80 and 81 which extend respectively within the pod sections 20b and 20a. The end of the conduit 80 which engages the section 20a is preferably provided with a shut-off valve (not shown) which shuts off air flow from the conduit 80 when the pod sections 20a and 20b are separated. Such control valve assemblies are known to those of skill in the art and no further description thereof is believed necessary.

Figure 10:
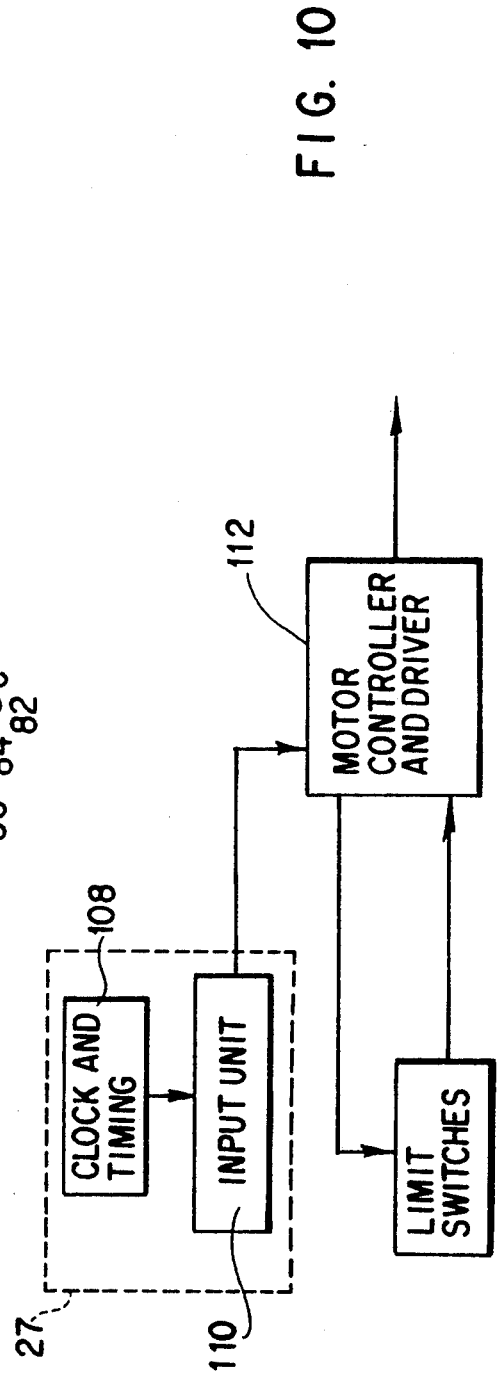
FIG. 10 is a schematic view of the control system for the sensor assembly.

Referring to FIG. 10, there is a schematic representation of the elements of the sensor controller 27. A clock and timing circuit 108 is utilized to supply control signals for the motor controller and driver 112. Clocked pulses cause the driver to drive the stepper motor in accordance with the number of pulses received.

In operation, the pod section 20a is connected to the pod section 20b and the sensor assembly 10 is strapped on a wrist of a subject. Thereafter, an optimum hold-down pressure is achieved by introducing air under pressure into the space defined by the housing and the rolling bellows 32. The hold-down pressure can be automatically determined by known systems, such as that described in U.S. Pat. No. 4,836,213 referenced above. Suitable control arrangements for varying the hold-down-pressure which can be utilized are described, for example in U.S. Pat. Nos. 4,951,679 and 4,966,156, the disclosures of which are incorporated by reference herein.

After the optimal hold-down pressure is determined and applied in the sensor assembly 10, further signal optimization is achieved by varying the position of the blood pressure sensor 62 with respect to the radial artery and the radius (bone) by advancing and retracting the sensor mounting member 46. The reasons for this can be appreciated by referring to FIG. 11. The hold-down pressure forces the sensor 62 and reference surface 56 against the subject's skin 121. The equilibrium position of the sensor assembly reference surface is determined primarily by the locations of the prominence of the radius 122 and the flexor carpi radialis tendon 123. These two structures are relatively rigid, compared to the skin 121, radial artery 124 and surrounding tissues. Thus, the degree of compression of the radial artery will be determined by the distance, d, that the sensor extends beyond the reference surface. For optimum measurement accuracy, the radial artery must be partially compressed (as shown in FIG. 11), but it must not be completely occluded.

Figure 11:
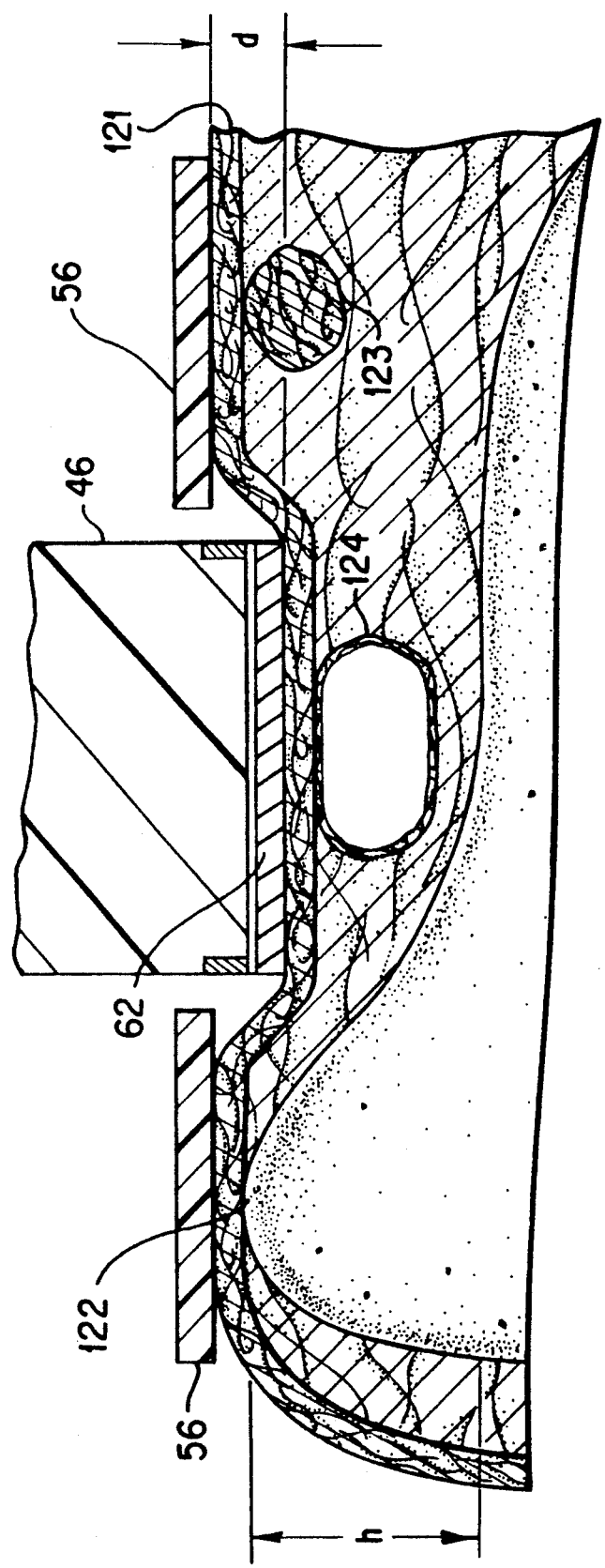
FIG. 11 is a cross-sectional view showing placement of a pressure sensor on a subject.

Still referring to FIG. 11, there are numerous anatomical variations between different subjects. In particular, the height, h, of the radial prominence 122 will differ. Thus, the value of d required for proper arterial compression of one subject might be (for example) 1 mm; while proper compression for another subject would be obtained with d=4 mm. The disclosed apparatus provides for proper arterial compression in nearly all subjects by providing adjustment of the extension distance, d, while the sensor assembly is being worn by the subject. The extension distance is changed or adjusted by applying a predetermined number of pulses from the clock and timing element 108 to the motor controller and driver 112 of the stepper motor M through the manual input unit 110. The number and direction of such pulses are controlled by manually settable counters and switches in the input unit 110. The clock and timing element 108 may be part of the sensor controller 27, as shown, or the controller may use clock signals from a clock and timing element which is a part of the central unit 26. Optimum extension of the sensor can be verified by the operator upon evaluation of the output displayed on, for example CRT 29 and can be achieved by changing the control values manually set in the manual input unit 110.

Figure 12:
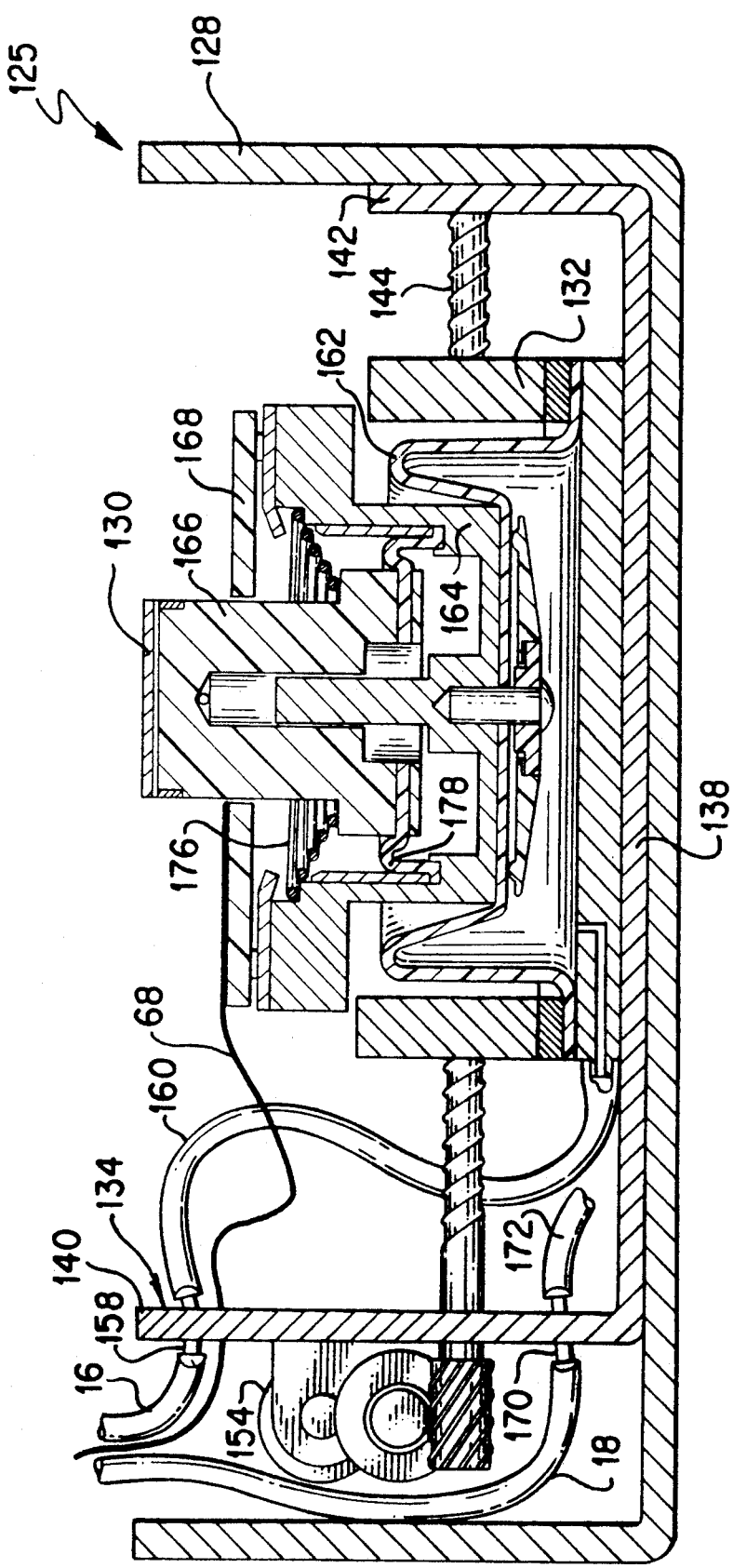
FIG. 12 is a cross-sectional view of a second embodiment of a sensor assembly, in which the sensor is laterally movable.
Figure 13:
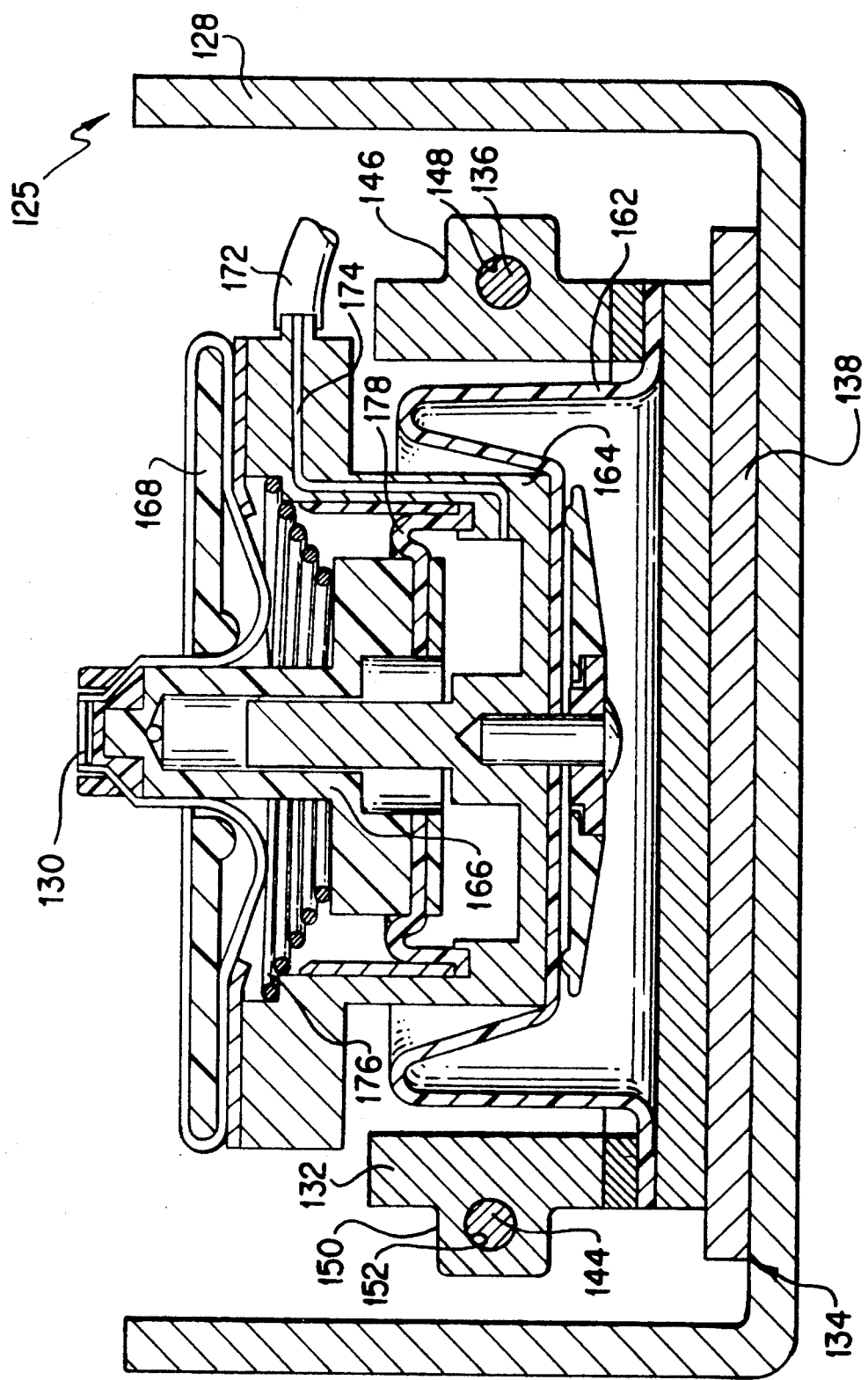
FIG. 13 is a cross-sectional view of the sensor assembly rotated 90° with respect to the cross-sectional view of FIG. 12.

A second embodiment of sensor assembly is illustrated in FIGS. 12 and 13. In this embodiment, the sensor assembly 125 includes an arrangement for allowing the sensor to be moved laterally with respect to the housing 128 to permit the optimization of the lateral position of pressure transducer 130 with respect to the subject. By providing for lateral movement of the pressure transducer 130, the transducer can be placed in a substantially central position with respect to the radial artery 124 (FIG. 11) of the subject. Similar arrangements and the benefits thereof are disclosed in U.S. Pat. No. 4,830,017, the disclosure of which is incorporated herein by reference.

The construction and operation of the portion of the sensor assembly of the FIG. 12 and 13 embodiment which provides for varying the hold-down pressure of the assembly and extension of the pressure transducer 30 is essentially the same as that previously described with respect to FIGS. 1–11. However, in this second embodiment, the housing 28 is replaced by a bellows cavity block 132, which is mounted for transverse movement with respect to the housing 128. A strap (not shown) or similar mounting means attached to the housing 128 is used for securing the sensor assembly 125 onto a subject.

As shown in FIG. 12, a transport frame 134 is mounted within the housing 128. The bellows cavity block 132 is movable longitudinally in the transport frame 134. In the arrangement illustrated in FIGS. 12 and 13, the transport frame 134 includes a guide shaft 136 located along one longitudinal edge of, and extending substantially parallel to, the base 138 of the transport frame. The ends of the guide shaft 136 are received in the end walls 140 and 142 of the transport frame. A lead screw 144 extends in a similar fashion along the opposite edge of the transport frame 134 and is rotatably mounted by the end walls 140 and 142. As shown in FIG. 13, the bellows cavity block 132 includes a boss 146 having a smooth bore 148 for slidably receiving the guide shaft 136. The opposite side of the bellows cavity block 132 includes a boss 150 having a threaded bore 152 for engaging the lead screw 144. Rotation of lead screw 144 moves the bellows cavity block and the associated pressure transducer mounting structure along the transport frame 134. The direction of rotation of the lead screw 144 determines the longitudinal direction of movement of the bellows cavity block 132.

An arrangement for rotating lead screw 144 includes a bi-directional motor 154 mounted on end wall 140 of the transport frame 134. Through a suitable gear train 155, rotation of the output of motor 154 is imparted to the lead screw 144, to move the cavity block 132. A control system for motor 154 is described in above noted U.S. Pat. No. 4,830,017 and such a system can be utilized in the second embodiment to effect optimal lateral postioning of the pressure transducer 130 automatically.

As illustrated in FIG. 12, in the second embodiment, the end wall 140 can include transition fittings for providing air and hydraulic fluid to the bellows block 132 and its associated components. As shown, the air line 16 is secured on fitting 158, which extends through end wall 140. The opposite side of fitting 158 receives a length of air hose 160 which is connected, through suitable porting, to the bellows cavity block 132. The hold-down pressure of the sensor assembly 125 is varied by application of air under pressure to the closed volume formed between the interior bottom surface of the bellows cavity block 132 and the bellows 162, which is secured in the bellows cavity block 132 and attached to the cavity block 164. In this manner, the subassembly comprising the cavity block 164, the sensor mounting member 166 and the cover plate/reference surface 168 is pressed against the skin surface of the subject in essentially the same manner as the embodiment illustrated in FIGS. 1-11.

A second transition fitting 170 is mounted in end wall 140 for providing a connection for hydraulic line 18 to a length of hydraulic line 172, which, as shown in FIG. 13 is connected to suitable porting 174 in the cavity block 164. In the same manner as described in connection with FIGS. 2-4, hydraulic fluid supplied to the cavity block 164 urges the transducer mounting member 166 out of the cavity block 164 against the bias of the helical spiral spring 176, as hydraulic fluid is introduced into the volume formed by the lower portion of the cavity block 164 and the rolling bellows 178. A system for controlling extension and retraction of the transducer mounting member 166 with respect to the reference surface is provided, which is essentially the same as that used in the embodiment illustrated in FIGS. 1-11.

The disclosed system provides many advantages which result in an overall reduction in the cost of the sensor assembly so that the sensor can be made disposable. By interposing the pod 20 between the control unit and the sensor assembly 10, disposability is enhanced. The use of the separable pod feature also allows more costly elements of the system, for example, the stepper motor and transmission, to be retained and reused and provides for less expensive components, such as the master cylinder, to be associated with the disposable part of the system. The rod-guided mounting of the pressure sensor piston 46 provides guidance of the mounting member 46, yet allows the use of a rolling bellows so that expensive close tolerance machining of the cavity block 30 and the sensor mounting member 46 is avoided. Further, the use of a spiral helical spring provides an open space adjacent the sensor piston 46 in which the loops of the flexible printed circuit may extend.

The description given above is provided for illustrative purposes and the invention claimed herein can be embodied in other designs.

What is claimed is:

1. A sensing assembly for sensing physiological parameters of a subject comprising:

a housing;
   means for mounting the housing on a subject;
   a reference surface; means for compliantly mounting the reference surface in the housing;
   a sensor;
   means for mounting the sensor relative to the reference surface for movement between a retracted position closer to the reference surface and an advanced position farther from the reference surface;
   means for varying the hold-down pressure of the reference surface and sensor on the subject;
   a fluid motor for advancing or retracting the sensor relative to the reference surface;
   a fluid pump for driving the fluid motor;
   conduit means for providing a path of fluid flow from the fluid motor to the pump;
   a drive means for driving the fluid pump;
   a pod comprising a first section; a second section; and means for detachably interconnecting the first section to the second section;
   means for mounting the fluid pump in the first section of the pod; and
   means for mounting the drive means in the second section of the pod.

2. Apparatus as in claim 1, wherein the means for mounting the sensor for movement relative to the reference surface comprises a guide rod and a sensor mounting member mounted for movement on the guide rod.

3. Apparatus as in claim 2, wherein the fluid motor moves the sensor mounting member.

4. Apparatus as in claim 1, wherein the drive means comprises a stepping motor.

5. Apparatus as in claim 4, wherein the output of the stepping motor is bidirectional.

6. Apparatus as in claim 1, wherein the sensor assembly comprises:

a cover plate forming said reference surface;
   an opening in the cover plate;
   a portion of the sensor mounting means extending away from the housing through the cover plate;
   means securing the sensor on the portion of the sensor mounting means extending through the cover plate;
   a flexible printed circuit for providing electrical connection to the sensor, said flexible printed circuit including a first portion connected to the sensor and extending from the sensor to the cover plate, a second portion extending from the first portion and forming a loop on one side of the cover plate and extending to an edge of the cover plate, and a third portion extending from the second portion about an edge of the cover plate and along an opposite side of the cover plate.

7. Apparatus as in claim 1, further comprising means for moving the sensor laterally with respect to the housing.

8. A sensor assembly for sensing physiological parameters of a subject comprising:

a housing;
   means for mounting the housing on a subject;
   a sensor means for detecting a physiological parameter of the subject;
   a reference surface, means for mounting the reference surface in the housing;
   sensor mounting means for mounting the sensor means for movement relative to the reference surface;

means for moving the sensor mounting means relative to the reference surface, said moving means comprising a fluid pump and a stepping motor for driving the fluid pump; and means for controlling the stepping motor to cause the sensor mounting means to move relative to the reference surface.

9. Apparatus as in claim 8, wherein the moving means further comprises:

a fluid motor;

means for mounting the fluid motor in the housing, said fluid motor being arranged to move the sensor mounting means; and a fluid conduit connecting the fluid pump to the fluid motor, whereby movement of the pump imparts movement to the fluid motor.

10. Apparatus as in claim 9, wherein said fluid conduit extends from the fluid motor, outside said housing, to said fluid pump.

11. Apparatus as in claim 10, further comprising:

a second housing, said second housing including first and second separable sections;

means mounting the fluid pump in the first separate section of said second housing;

means mounting the stepping motor in said second separable section of said second housing; and means for providing a driving connection between the fluid pump and the stepping motor when the separable sections of said second housing are joined.

12. Apparatus as in claim 8, wherein the fluid pump comprises a movable element for pressurizing fluid;

a drive means for transmitting movement of the stepping motor to the movable element.

13. Apparatus as in claim 12, wherein the movable element comprises a piston movable in a cylinder and the drive means comprises a helically grooved shaft and means carried by the piston for engaging the grooved shaft; and wherein the stepping motor is a rotary motor.

14. Apparatus as in claim 8, further comprising means for moving the sensor mounting means laterally with respect to the housing.

15. A sensing assembly for sensing a physiological parameter of a subject comprising:

a housing;

a sensor for detecting a physiological parameter of a subject;

means for movably mounting the sensor in the housing, said movable mounting means comprising means defining a fluid cavity;

an upstanding rod mounted in the cavity;

a movable sensor mounting member slidably received on the rod; and biasing means for biasing the sensor mounting member in a retracted position relative to the housing.

16. Apparatus as in claim 15, further comprising a rolling bellows cooperative between the fluid cavity and the sensor mounting member for forming a fluid chamber.

17. Apparatus as in claim 15, wherein a second cavity is formed between the distal end of the rod and the sensor mounting means and further comprising means for providing fluid communication between the fluid cavity and said second cavity.

18. Apparatus as in claim 15, further comprising:

means for securing the housing on a subject;

a reference surface; and means for varying the hold-down pressure of the reference surface and the sensor on the subject.

19. Apparatus as in claim 18, wherein the means for varying the hold-down pressure comprises a gas-pressurized chamber cooperative between the housing and said fluid cavity defining means.

20. Apparatus as in claim 15, wherein the biasing means comprises a compression spring.

21. Apparatus as in claim 20, further comprising:

a cover plate mounted on said means defining a fluid cavity, said cover plate having an opening therein;

said sensor mounting member having a portion thereof extending through the opening;

means mounting the sensor on the portion of the sensor mounting member extending through said opening; and flexible electrical connection means for providing electrical connection to the sensor, the connection means having a first portion extending from the sensor to a location on one side of the cover plate, a second portion extending in a loop formed near said one side of the cover plate from the first portion to an edge of the cover plate and a third portion in electrical connection with the second portion and extending along the side of the cover plate opposite said one side.

22. Apparatus as in claim 21, wherein the electrical connection means comprises a flexible printed circuit.

23. Apparatus as in claim 21, wherein the spring is located outwardly of the looped portion of the electrical connection means, to provide space for the loop formed by the second section.

24. Apparatus for mounting a physiological sensor to a supporting structure comprising:

a sensor;

a sensor support member;

means mounting the sensor on the sensor support member;

a flexible printed circuit for providing electrical connections to the sensor;

means for providing electrical and mechanical attachment of the flexible printed circuit to the sensor;

a guard member attached to said sensor support member, for protecting the sensor mounting means and a portion of said flexible printed circuit;

a clamping means for clamping said flexible printed circuit between said guard member and said sensor support member; and a fold or undulation in said flexible printed circuit, said fold being located between said attachment means and said clamping means.

25. Apparatus as in claim 24, further comprising a layer of an elastomeric material overlying the sensor and the attachment means.

* * * * *